United States Patent [19]

Jakobson et al.

[11] Patent Number: 4,960,953

[45] Date of Patent: Oct. 2, 1990

[54] PROCESS FOR PREPARING POLYGLYCEROLS

[75] Inventors: Gerald Jakobson; Werner Siemanowski, both of Rheinberg, Fed. Rep. of Germany

[73] Assignee: Deutsche Solvay-Werke GmbH, Solingen, Fed. Rep. of Germany

[21] Appl. No.: 328,316

[22] Filed: Mar. 24, 1989

[30] Foreign Application Priority Data

Mar. 24, 1988 [DE] Fed. Rep. of Germany ....... 3809882

[51] Int. Cl.$^5$ ...................... C07C 07/70; C07C 41/03; C07C 29/76
[52] U.S. Cl. .................................. 568/621; 568/619; 568/120; 568/623; 568/679; 568/680; 568/870
[58] Field of Search ............... 568/619, 620, 621, 623, 568/679, 680, 870

[56] References Cited

U.S. PATENT DOCUMENTS 2,520,670 8/1950 Wittcoff et al. ..................... 260/615

FOREIGN PATENT DOCUMENTS 44-26672 11/1969 Japan .

Primary Examiner—Howard T. Mars
Attorney, Agent, or Firm—Foley & Lardner, Schwartz, Jeffery, Schwaab, Mack, Blumenthal & Evans

[57] ABSTRACT

A process for the preparation of polyglycerols which are low in cyclic components comprises reacting glycerol or diglycerol or a higher polyglycerol with epichlorohydrin at elevated temperatures; adding base corresponding to the organically bound chlorine content of the reaction mixture, at a temperature of 50°–120° C., to the unseparated reaction mixture obtained; desalting the resultant reaction mixture and recovering glycerol, diglycerol and higher polyglycerols by fractional distillation.

31 Claims, No Drawings

PROCESS FOR PREPARING POLYGLYCEROLS

BACKGROUND OF THE INVENTION

The present invention relates to a process for preparing polyglycerols which are low in cyclic components.

U.S. Pat. No. 2,520,670 discloses a process for the preparation of polyglycerols in which glycerol is reacted with glycerol α-monochlorohydrin in the presence of concentrated alkali at elevated temperature to form a mixture of polyglycerols. This process has the disadvantage of a relatively long reaction duration and requires that the reaction mixture be worked up using lower aliphatic alcohols when the reaction is complete. Details on the polyglycerol yields achieved and on their cyclic component content are not given.

OBJECTS OF THE INVENTION

One object of the present invention is to provide a process in which polyglycerols are obtained in good yields and with only a low content of cyclic components. Another object of the invention is to provide a process for producing polyglycerols whereby it is unnecessary to isolate the intermediates (chlorohydrin/ether mixture).

A further object of the invention is to provide a process for producing polyglycerols in which, for environmental protection reasons, it is possible to avoid workup of the end products by treatment with organic solvents.

SUMMARY OF THE INVENTION

It has now been found according to the invention that these objects are achieved by a process for preparing polyglycerols which are low in cyclic components, which comprises the steps of:

(a) reacting glycerol, diglycerol, a higher polyglycerol or a mixture thereof with epichlorohydrin, at a temperature of from 90° C. to 170° C., in a molar ratio of glycerols to epichlorohydrin of from 5:1 to 1:3, to produce a crude chlorohydrin/ether mixture;

(b) adding to the crude chlorohydrin/ether mixture, at a temperature of from 50° C. to 120° C., an amount of a strong base at least substantially equivalent to the organically bound chlorine content of the chlorohydrin/ether mixture, to produce a crude glycerols mixture;

(c) desalting the crude glycerols mixture, and recovering substantially purified glycerol, diglycerol and higher polyglycerols fractions.

In a preferred embodiment, the crude glycerols mixture is diluted with water and desalted using ion exchangers, after which water is distilled out and the resultant glycerols mixture is fractionally distilled.

DETAILED DESCRIPTION

For purposes of this discussion, the term "polyglycerol" denotes diglycerol, triglycerol, tetraglycerol and higher oligomeric glycerol polyethers. The term "higher polyglycerol" denotes triglycerol, tetraglycerol, pentaglycerol, and higher oligomers but not diglycerol. The term "glycerols" includes both glycerol and polyglycerols.

According to the process of the invention, glycerol, diglycerol, a higher polyglycerol or a mixture thereof is reacted with epichlorohydrin (instead of chlorohydrin) at temperatures of from 90° C. to 170° C., preferably 120° C. to 150° C., in a molar ratio between glycerol or diglycerol or higher polyglycerol and epichlorohydrin of from 5:1 to 1:3; a strong base, preferably an alkaline aqueous solution, is added at a temperature of from 50° C. to 120° C., preferably 80° C. to 95° C., to the unseparated reaction mixture obtained, the amount of base corresponding to the organically bound chlorine content of the reaction mixture; generally, water is added, the reaction mixture is desalinated, e.g., by using one or more cation exchangers and subsequently using anion exchangers, water is removed by distillation, and the glycerol/ polyglycerol mixture is separated into glycerol, diglycerol and higher polyglycerols by fractional distillation.

According to an advantageous embodiment of the invention, the crude chlorohydrin/ether mixture from step (a) is diluted to an approximately 70%–40% strength by weight (% by weight of glycerols), preferably 60%–50% strength by weight, solution by addition of water and desalinated with a combination of strongly acidic cation exchangers and subsequently weakly basic anion exchangers at temperatures of from 30° C. to 80° C., preferably 40° C. to 60° C.

Strongly acidic cation exchangers are conventional and normally use a cation exchange resin with strong acid groups thereon, e.g., crosslinked polystyrene bearing sulfonic acid groups thereon. Weakly basic anion exchangers are also well known and normally use an anion exchange resin with weakly basic groups thereon, e.g., crosslinked polystyrene bearing tertiary amine (e.g., diethylamino, dimethylaminomethyl and the like) groups thereon.

The strong base can in principle be any material which is strongly alkaline and which is compatible with the other reactants in the crude chlorohydrin/ether mixture. Preferably, the strong base is an aqueous alkaline solution, e.g., a solution of an alkali metal hydroxide, carbonate or like basic anion. According to a preferred embodiment, an alkaline alkali metal carbonate solution, preferably a concentrated sodium carbonate solution, is added to the unseparated reaction mixture from the reaction of epichlorohydrin with glycerol, diglycerol or a higher polyglycerol.

The alkaline alkali metal carbonate solution is advantageously added to the crude reaction mixture from the reaction of epichlorohydrin with glycerol, diglycerol or a higher polyglycerol in at least a substantially equivalent ratio between alkali metal carbonate and the organically bound chlorine content of from about 1:1 to about 1.2:1, preferably 1.05:1 to 1.1:1.

The pH of the reaction mixture is expediently adjusted to the range 7.0 to 11.5, preferably 8 to 11, by addition of the alkaline aqueous solution.

According to a further embodiment, the reaction mixture is cooled to room temperature, and the majority of the precipitated salt is separated off, preferably filtered off, prior to ion exchange desalination.

If necessary, the desired composition of the polyglycerol mixture can be varied according to the invention by varying the molar ratio between glycerol and epichlorohydrin and by using diglycerol or higher polyglycerols instead of glycerol.

Thus, in order to increase the diglycerol proportion, the molar ratio between glycerol and epichlorohydrin is 4:1 to 2.5:1, according to one embodiment.

According to a further embodiment, in order to increase the polyglycerol proportion produced in addition to diglycerol, the molar ratio between glycerol and/or diglycerol and epichlorohydrin is 2.49:1 to 0.5:1, preferably 1.8:1 to 0.4:1.

According to another embodiment, the alkaline alkali metal carbonate solution is added in a slight excess to the unseparated reaction mixture from the reaction of epichlorohydrin with glycerol, diglycerol or a higher polyglycerol, and this excess is neutralized when the reaction is complete.

Hydrochloric acid is preferably employed for the neutralization, but it is also possible to use other mineral acids or acidic cation exchangers.

It has furthermore been determined according to the invention that a change in the molar ratio is accompanied by a change in the reaction time. It has been shown that, with respect to the reaction time, and the minimum cyclic component content desired in the crude polyglycerol mixture, a molar ratio between glycerol and/or diglycerol and epichlorohydrin of from 2.5:1 to 1.0:1 has proven particularly suitable.

The regeneration of the cation exchange resin in the cation exchangers is preferably carried out by means of cocurrent or combined cocurrent regeneration.

According to a preferred embodiment, the salts are washed out after the regeneration. When the washing-out process is complete, a concentrated polyglycerol-containing, preferably diglycerol-containing solution is passed through the ion exchanger, and the polyglycerol-containing, preferably diglycerol-containing solution leaving the anion exchanger is recycled until a polyglycerol content, preferably a diglycerol content, of 20% by weight is achieved, preferably until a polyglycerol content, preferably a diglycerol content, of 15% by weight is achieved. This solution can be used to dilute the reaction product of step (b) to prepare the 70%–40% strength by weight, preferably 60%–50% strength by weight, polyglycerol-containing, preferably diglycerol-containing starting solution for desalination.

The polyglycerol-containing, preferably diglycerol-containing solution is preferably passed through the ion exchangers under superatmospheric pressure in step (c).

In this case, the polyglycerol-containing, preferably diglycerol-containing solution is passed through the ion exchangers, i.e., through one or more cation exchangers and at least one anion exchanger, under a pressure of 1.1–10 bar, preferably 2–6 bar. Valves are installed at one or more points in the line or in the ion exchangers in order to control and maintain the pressure.

In this case, the polyglycerol-containing, preferably diglycerol-containing solution is expediently passed through the ion exchangers at a flow rate of from 0.5 m/h to 15 m/h, preferably 1 m/h to 5 m/h.

The cation exchange resin and anion exchange resin preferably used are those which are temperature-stable to at least about 80° C., preferably to at least about 100° C.

The ion exchange resins of the cation exchanger and/or anion exchanger are expediently covered by a sieve plate, perforated plate or a device which is arranged movably in the height direction of the ion exchanger, covers the exchanger composition and enables a uniform rate of liquid passage, and/or an inert compressed composition and/or an elastic plastic composition, the latter two being preferably in granular form. All of the foregoing are conventional means to avoid channeling and eddying that would disturb or erode the resin bed of the column and interfere with optimal contact between the fluid stream and the resin.

The strongly acidic cation exchange resin and the weakly basic anion exchange resin each preferably have an internal surface area (measured by the BET method) of greater than 25 $m^2/g$, preferably 50 to 100 $m^2/g$.

The following examples illustrate the process of the invention but are not limitative thereof.

EXAMPLE 1

Preparation of polyglycerol having a relatively high content of diglycerol 1.474 kg (16 mol) of glycerol and 740 g (8 mol) of epichlorohydrin are introduced into a 2 twin-walled reactor (heating liquid: oil). The two-phase reaction mixture is heated to boiling (reflux) with stirring. After about 80 minutes, the oil flow temperature is increased to about 145° C., unreacted epichlorohydrin again refluxing. After 50 minutes at an oil flow temperature of 145° C., the latter is reduced to 140° C. It is thus possible to stop the slightly exothermic reaction and to keep the reaction temperature at 150° C. The oil flow temperature and the temperature of the reaction solution had equalize after about 50 minutes. The reaction is complete after a total of 3.25 hours.

Crude product weight: 2.205 kg = 1.75 l.

1.284 kg (organically bound chlorine = 4.776 mol) of this crude chlorohydrin/ether mixture are introduced into the same reactor and warmed to 90° C. 1.125 l (corresponding to the organically bound chlorine content plus an excess of 5%) of a 2.23 molar sodium carbonate solution are added at 90° C. over the course of 1 hour (moderate $CO_2$ evolution). After a further 1.5 hours at this temperature, the heating is removed and the reaction batch is neutralized by addition of ½ concentrated hydrochloric acid.

Crude product weight: 2.516 kg

Final volume: about 2.15 l

The neutral reaction solution is diluted with water, the mixture is desalinated via a combination of strongly acidic cation exchangers and slightly basic anion exchanger, and the water is removed by evaporation in vacuo.

Final product weight: 1.040 kg

The product mixture has the following composition in % by weight: glycerol 43.5, cyclic diglycerol 0.9, diglycerol 38.5, cyclic triglycerol 0.4, triglycerol 11.8, cyclic tetraglycerol 0.1, tetraglycerol 3.0, pentaglycerol 0.7, hexaglycerol 0.1.

EXAMPLES 2–4

The procedure of Example 1 is repeated using different ratios of glycerol to epichlorohydrin.

Values obtained for the polyglycerol mixture in % by weight on changing the glycerol:epichlorohydrin molar ratio 1:1 (Example 2), 2:1 (Example 1), 3:1 (Example 3) and 1:2 (Example 4), are shown below.

|  | Ex. 2 1:1 | Ex. 1 2:1 | Ex. 3 3:1 | Ex. 4 1:2 |
| --- | --- | --- | --- | --- |
| Glycerol | 25.4 | 43.5 | 53.6 | 37.2 |
| Cyclic diglycerol | 1.5 | 0.9 | 1.2 | 1.5 |
| Diglycerol | 42.4 | 38.5 | 33.1 | 41.7 |
| Cyclic triglycerol | 1.0 | 0.4 | — | 0.8 |
| Triglycerol | 19.6 | 11.8 | 8.4 | 13.6 |
| Cyclic tetraglycerol | 0.9 | 0.1 | 0.7 | 0.5 |
| Tetraglycerol | 5.7 | 3.0 | 1.8 | 3.1 |
| Pentaglycerol | 2.4 | 0.7 | 0.6 | 1.0 |
| Hexaglycerol | 0.6 | 0.1 | — | — |

EXAMPLE 5

Preparation of polyglycerol having a relatively high content of triglycerol 664.6 g (4 mol) of diglycerol and 185 g (2 mol) of epichlorohydrin are introduced into a 1 1 twin-walled reactor (heating liquid: oil). The two-phase reaction mixture is heated to boiling (reflux, bath temperature 130° C.) with stirring. After about 1 hour, the oil flow temperature is increased to 145° C. and kept at this temperature for about 2 hours.

The reaction is complete after a total of about 3 hours.

Crude product weight: 849 g=0.7 1

784.9 g (organically bound chlorine=1.848 mol) of this crude chlorohydrin/ether mixture are introduced into a 2 1 twin-walled reactor and warmed to 90° C.. 485 ml of a 2 molar sodium carbonate solution are added at 90° C. over the course of about 45 minutes (moderate $CO_2$ evolution). After a further 1.5 hours at this temperature, the heating is removed and the reaction batch is neutralized by addition of ½ concentrated hydrochloric acid.

Crude product weight: 1.315 kg–1.15 1

The neutral reaction solution is diluted with water, the mixture is desalinated via a combination of strongly acidic cation exchangers and slightly basic anion exchangers, and the water is removed by evaporation in vacuo.

Final product weight: 715 g.

The product mixture has the following composition in % by weight:

glycerol 4.9, cyclic diglycerol 0.1, diglycerol 50.8, cyclic triglycerol 2.1, triglycerol 25.6, cyclic tetraglycerol 0.5, tetraglycerol 4.9, pentaglycerol 6.0, hexaglycerol 3.5, heptaglycerol 0.8 and octaglycerol 0.1.

What is claimed is:

1. A process for preparing polyglycerols which are low in cyclic components, which comprises the steps of:
   (a) reacting glycerol, diglycerol, a higher polyglycerol or a mixture thereof with epichlorohydrin, at a temperature of from 90° C. to 170° C., in a molar ratio of glycerols to epichlorohydrin of from 5:1 to 1:3, to produce a crude chlorohydrin/ether mixture;
   (b) adding to the crude chlorohydrin/ether mixture, at a temperature of from 50° C. to 120° C., an amount of an alkaline medium substantially equivalent to the organically bound chlorine content of the chlorohydrin/ether mixture, to produce a crude glycerols mixture; and
   (c) desalting the crude glycerols mixture by diluting said mixture with water and passing the resultant diluted aqueous glycerols solution first through one or more cation exchangers and then through one or more anion exchangers, to produce a substantially desalted aqueous glycerols solution, and recovering substantially purified glycerol, diglycerol and higher polyglycerols fractions.

2. A process according to claim 1, wherein products are recovered by removing water from said desalted aqueous glycerols solution by distillation and separating the resultant glycerol/polyglycerol mixture into glycerol, diglycerol and higher polyglycerols by fractional distillation.

3. A process according to claim 1, wherein in step (c), said crude glycerols mixture is diluted to a 70%–40% strength by weight glycerols solution.

4. A process according to claim 3, wherein in step (c), said crude glycerols mixture is diluted to a 60%–50% strength by weight glycerols solution.

5. A process according to claim 1, wherein in step (c), said cation exchanger contains a strongly acidic cation exchange resin and said anion exchanger contains a weakly basic anion exchange resin.

6. A process according to claim 5, wherein said diluted glycerols solution is passed through said ion exchangers at a temperature of from 30° C., to 80° C.

7. A process according to claim 6, wherein said temperature is from 40° C. to 60° C.

8. A process according to claim 1, wherein in step (b), said alkaline medium is an alkali metal carbonate solution.

9. A process according to claim 8, wherein said alkali metal carbonate solution is a concentrated sodium carbonate solution.

10. A process according to claim 1, wherein in step (b), the ratio of said alkaline medium to said organically bound chlorine is form 1:1 to 1.2:1.

11. A process according to claim 10, wherein said ratio is from 1.05:1 to 1.1:1.

12. A process according to claim 1, wherein in step (b), the pH of the reaction mixture is adjusted to the range 7.0 to 11.5 by addition of said alkaline medium.

13. A process according to claim 12, wherein said pH is in the range 8 to 11.

14. A process according to claim 1, wherein in step (c), said crude glycerols mixture is cooled to room temperature, and the majority of the salt precipitated is physically separated off as a solid, after which the remaining liquid is desalted.

15. A process according to claim 1, wherein in step (a), the molar ratio between glycerol and epichlorohydrin is 4:1 to 2.5:1, thereby resulting in a higher proportion of diglycerol in the product mixture.

16. A process according to claim 1, wherein regeneration of the cation exchanger resin in the cation exchangers is carried out by cocurrent or combined cocurrent regeneration.

17. A process according to claim 16, wherein the salts are washed out after the regeneration, and wherein after completion of the washing-out process, a glycerols solution is passed through the ion exchanger, passed through the anion exchanger, and recycled until its glycerols content is reduced to about 20% by weight.

18. A process according to claim 17, wherein the glycerols content of said recycled solution is reduced to about 15% by weight.

19. A process according to claim 17, wherein said recycled solution, after reduction of the glycerols content thereof, is used with water in step (c) to dilute said crude glycerols mixture to 70–40% strength by weight, prior to desalting by cationic and anionic exchangers.

20. A process according to claim 1, wherein said diluted aqueous glycerols solution is passed through the ion exchangers under a superatmospheric pressure.

21. A process according to claim 20, wherein said pressure is 1.1–10 bar.

22. A process according to claim 21, wherein said pressure is 2–6 bar.

23. A process according to claim 1, wherein the ion exchange resins in each cation exchanger and anion exchanger are provided with permeable covering means to ensure a uniform rate of liquid passage through said resin.

24. A process according to claim 6, wherein said cation exchanger resin and said anion exchanger resin are each temperature stable to at least 80° C.

25. A process according to claim 24, wherein said resins are each temperature stable to at least 100° C.

26. A process according to claim 6, wherein said strongly acidic cation exchange resin and said weakly basic anion exchange resin each have an internal surface area (measured by the BET method) of greater than 25 m$^2$/g.

27. A process according to claim 26, wherein said internal surface area is from about 50 to about 100 m$^2$/g.

28. A process according to claim 1, wherein in step (c), said diluted aqueous glycerols solution is passed through said ion exchangers at a flow rate of from 0.5 m/h to 15 m/h.

29. A process according to claim 28, wherein said flow rate is from 1 m/h to 5 mh.

30. A process according to claim 1, wherein in step (a), said temperature is 120° C. to 150° C.

31. A process according to claim 1, wherein in step (b), said temperature is 80° C. to 95° C.

* * * * *